US00PP23479P2

(12) United States Plant Patent
Striem et al.

(10) Patent No.: US PP23,479 P2
(45) Date of Patent: Mar. 19, 2013

(54) GRAPEVINE PLANT NAMED 'SUGRAFORTY'

(50) Latin Name: *Vitis vinifera*
Varietal Denomination: Sugraforty

(75) Inventors: Michael J. Striem, Rehovot (IL); Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 13/374,275

(22) Filed: Dec. 20, 2011

(51) Int. Cl.
*A01H 5/00* (2006.01)

(52) U.S. Cl. ..... Plt./205

(58) Field of Classification Search ..... Plt./205
See application file for complete search history.

*Primary Examiner* — Annette Para
(74) *Attorney, Agent, or Firm* — Knobbe, Martens, Olson & Bear, LLP

(57) ABSTRACT

A new and distinct grapevine variety characterized by producing uniform, oval, black, berries. The berries have a medium sugar content and a slightly fruity flavor. Harvest of the new variety starts 7-10 days earlier than harvest of the comparable variety 'Summer Royal' (unpatented).

1 Drawing Sheet

Latin name of the genus and species claimed: *Vitis vinifera*.
Variety denomination: 'SUGRAFORTY'.

BACKGROUND AND SUMMARY OF THE INVENTION

This invention relates to the discovery and asexual propagation of a new and distinct variety of grapevine, 'Sugraforty', as herein described and illustrated. The new variety originated by controlled hybridization. The new variety was first hybridized in 2008 by Michael Striem in Wasco, Kern County, Calif., and was selected from a population of hybrid seedlings by Terry Bacon in 2010.

The new variety Sugraforty' is characterized by producing oval black berries ripening very early in the season. The berries of 'Sugraforty' are firm, slightly juicy, have medium sugar content and a slightly fruity flavor.

The seed parent is the varietal selection '02014-168-033' (unpatented) and the pollen parent is the varietal selection '04017-201-252' (unpatented). The parent varieties were first crossed in May 2008 by Michael Striem. The date of first sowing was March 2009, and the date of first flowering was May 2010.

The new variety 'Sugraforty' was first asexually propagated in December 2010, in Wasco, Kern County, Calif., by Terry Bacon using hardwood cuttings.

The new variety 'Sugraforty' differs from its seed parent '02014-168-033' (unpatented) in that the fruit of the seed parent is seeded while the fruit of the new variety has rudimentary seeds. The new variety Sugraforty' resembles its seed parent in that both have oval black berries of about 5.1 g that ripen very early in the season.

The new variety Sugraforty' differs from its pollen parent '04017-201-252' (unpatented) in that the new variety has oval berries compared to elongated berries for the pollen parent. The berry size for new variety is also larger at about 5.1 g compared to about 2.5 g for the pollen parent. The cluster size is larger in the new variety at about 600 g compared to about 150 g for the pollen parent. The new variety 'Sugraforty' resembles its pollen parent in that they both have black berries that ripen very early in the season.

The new variety 'Sugraforty' resembles commercially-available USDA variety 'Summer Royal' (unpatented) in that both have black berries that ripen very early in the season. However, the new variety has an oval berry while 'Summer Royal' has a round-oval shape. In addition, the harvest of the new variety starts about 7-10 days earlier than 'Summer Royal' (unpatented). The new variety 'Sugraforty' also resembles 'Sugrathirteen' (PP104340) in that both have black berries. However, the new variety has oval shaped berries compared to the long-elliptic berries of 'Sugrathirteen'.

The new 'Sugraforty' variety has been shown to maintain its distinguishing characteristics through successive asexual propagations by, for example, rooted cuttings.

Variations of the usual magnitude from the characteristics described herein may occur with changes in any of a variety of factors such as growing conditions, irrigation, fertilization, pruning, management and with climatic variation.

BRIEF DESCRIPTION OF THE DRAWING

The accompanying color photographic illustrate FIG. 1 shows in full color a typical cluster of berries, a young shoot, and a mature leaf blade of the new grapevine 'Sugraforty'. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England (2000).

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugraforty' plants grown in the vicinity of Wasco, Kern County, Calif. during 2011, and is believed to apply to plants of the variety grown under similar conditions of soil and climate elsewhere.

VINE

General:

*Planting*.—Trained to a modified gable trellis, planted in about 7 ft.×12 ft. spacing.

*Practices*.—Gene-pool-vine: Spur-pruned to approximately 36 spurs per vine. Test-vines: Spur-pruned to approximately 36 spurs per vine.

*Size*.—Medium. Height: Approximately 2.0 m. Width: Approximately 2.2 m.

*Vigor*.—Vigorous.

*Fresh pruning weight*.—Approximately 7 kg per vine.

*Density of foliage*.—Dense.

*Productivity*.—Very productive — approximately 40 clusters per vine after thinning.

*Yield*.—Approximately 24 kg per vine.

*Crop load*.—Approximately 3.4 kg per vine (kg fruit per kg fresh-pruning-weight).

*Root stock*.—Not applicable.

*Own root*.—Yes.

*Resistance*.—Neither resistance nor susceptibility to diseases or pests has been observed in this variety.

Trunk:

*Shape*.—Circular.

*Diameter*.—Approximately 88 mm.

*Straps*.—Short.

*Surface texture*.—Shaggy.

*Inner bark color*.—Near Dark Grey Orange 165A.

*Outer bark color*.—Near Dark Greyed-green 197A and Near Medium Grey 201A.

SHOOTS

Young shoot:

*Form of tip*.—Half open.

*Distribution of anthocyanin coloration of tip*.—Striped.

*Intensity of anthocyanin coloration of tip*.—Weak.

*Density of prostrate hairs on tip*.—Medium.

*Density of erect hairs on tip*.—Absent.

Woody shoot (mature canes):

*Shape*.—Slender.

*Internode length*.—Approximately 60 mm.

*Width at node*.—Approximately 11 mm.

*Cross section*.—Circular.

*Surface*.—Smooth.

*Main color*.—Light Brown, about Medium Greyed-Orange 164B to Near Light Greyed-Yellow 161A.

*Lenticels*.—Absent.

*Density of erect hairs on nodes*.—Absent or Very Sparse.

*Density of erect hairs on internodes*.—Absent or Very Sparse.

*Growth of auxiliary shoots*.—Medium; Average 17.5 cm/shoot.

Flowering shoot:

*Vigor during flowering*.—Strong.

*Attitude during flowering on shoots which are not tied*.—Semi-erect.

*Color of dorsal side of internodes*.—Green with Red Highlights, about Medium Yellow-Green 144A and Dark Greyed-Purple 187A.

*Color of ventral side of internodes*.—Green with Red Highlights, about Medium Yellow-Green 144A and Dark Greyed-Purple 187A.

*Color of dorsal side of nodes*.—Green with Red Highlights, about Medium Yellow-Green 144A and Dark Greyed-Purple 187A.

*Color of ventral side of nodes*.—Green with Red Highlights, about Medium Yellow-Green 144A and Dark Greyed-Purple 187A.

*Density of erect hairs on nodes*.—Absent.

*Erect hairs on internode*.—Absent.

*Density of prostrate hairs on nodes*.—Absent.

*Density of prostrate hairs on internodes*.—Absent.

*Anthocyanin coloration of buds*.—Absent.

Tendrils:

*Distribution on the shoot at full flowering*.—Discontinuous.

*Thickness*.—Medium.

*Color*.—Near Medium Yellow-Green 144C.

*Form*.—Bifurcated.

*Number of consecutive tendrils*.—Up to 2.

*Length of tendril*.—Long, approximately 17 cm.

LEAVES

Young leaves:

*Color of upper surface of first 4 distal unfolded leaves*.—Green.

*Average intensity of anthocyanin coloration of six distal leaves prior to flowering*.—Absent.

*Density of prostrate hairs between veins at lower surface of 4th distal unfolded leaf*.—Absent.

*Density of erect hairs between veins at lower surface of 4th distal unfolded leaf*.—Absent.

*Density of prostrate hairs on veins at lower surface of 4th distal unfolded leaf*.—Absent.

*Density of erect hairs on veins at lower surface of 4th distal unfolded leaf*.—Absent.

Mature leaves:

*Average length*.—Approximately 130 mm.

*Average width*.—Approximately 160 mm.

*Size of blade*.—Medium.

*Shape of blade*.—Pentagonal.

*Number of lobes*.—Approximately 5.

*Anthocyanin coloration of main veins on the upper side of the blade*.—Absent.

*Mature leaf profile*.—Flat.

*Blistering surface of blade upper surface*.—Absent.

*Leaf blade tip*.—In the plane of the leaf.

*Undulation of margin*.—Slight.

*Thickness*.—Medium.

*Undulation of blade between main and lateral veins*.—Absent.

*Shape of teeth*.—Concave on both sides.

*Length of teeth*.—Medium, usually 5 to 15 mm, average 10 mm.

*Ratio length/width of teeth*.—Small.

*General shape of petiole sinus*.—Slightly open.

*Tooth at petiole sinus*.—Absent.

*Petiole sinus limited by veins*.—Absent.

*Shape of upper lateral sinus*.—Open.

*Depth of upper lateral sinus*.—Very Shallow.

*Density of prostrate hairs between veins on lower surface of blade*.—Absent.
*Density of erect hairs between veins on lower surface of blade*.—Absent.
*Density of prostrate hairs on main veins on lower surface of blade*.—Absent.
*Density of erect hairs on main veins on lower surface of blade*.—Absent.
*Density of prostrate hairs on main veins on upper surface of blade*.—Absent.
*Autumn coloration of leaves*.—Green, to Medium Yellow, about 11A, to Reddish-Brown About 178C in late November.

Upper surface:
*Color*.—Near Dark Green 139A.
*Surface texture*.—Smooth.
*Surface appearance*.—Dull.
*Glossiness*.—Weak.
*Pubescence*.—Absent.

Lower surface:
*Color*.—Near Dark Green 137A.
*Anthocyanin coloration of main veins on lower leaf surface*.—Absent.
*Glossiness*.—Weak.
*Pubescence*.—Absent.
*Surface texture*.—Smooth.
*Surface appearance*.—Dull.

Petiole:
*Length of petiole*.—Medium, Approximately 10 cm.
*Length of petiole compared to middle vein*.—Much shorter.
*Diameter*.—Approximately 4 mm.
*Density of prostrate hairs on petiole*.—Absent.
*Density of erect hairs on petiole*.—Absent.
*Shape of base of petiole sinus*.—U-shaped.
*Color*.—Light Red 39C and Medium Greyed-Red 182B.

Buds:
*Shape*.—Conical.
*Size*.—Medium, approximately 3 mm×4 mm.
*Position*.—Slightly held out.
*Cane bud fruitfulness*.—Basal most fruitful, $3^{rd}$ to $5^{th}$ bud position.
*Time of bud burst*.—Early, about March 11th.

FLOWERS

General:
*Flower sex*.—Hermaphrodite.
*Length of first inflorescence*.—Medium.
*Position of first flowering node*.—Fifth node.
*Number of inflorescences per shoot*.—Approximately 1 to 2.
*Date of full bloom*.—Approximately May 8th.
*Size (diameter of fully open flower)*.—Medium, approximately 6 mm.

FRUIT

General:
*Ripening period*.—Early, approximately July 1-14.
*Use*.—Table grapes.
*Keeping quality*.—Good.
*Shipping quality*.—Good.
*Date of first harvest*.—Approximately July 1st.
*Solids-sugar*.—Medium.
*Refractometer test*.—Approximately 17%.
*Acid*.—Medium, approximately 0.55 gr./L tartaric acid.
*Juice pH*.—Approximately 3.4.
*Tendency to crack*.—Low.
*Sensitivity to sunburn*.—Medium.
*Fruit shrivel after ripe*.—Absent.
*Secondary cluster*.—Occasioanl.
*Resistance*.—Absent.

Cluster:
*Bunch size (peduncle excluded)*.—Medium.
*Bunch length (peduncle excluded)*.—Medium, approximately 20 cm.
*Bunch width*.—Approximately 15 cm.
*Bunch weight*.—Medium, approximately 600 g.
*Bunch density*.—Medium.
*Number of berries*.—Approximately 112.
*Form*.—Conical-shaped.

Peduncle:
*Length of peduncle*.—Medium, approximately 40 mm.
*Lignification of peduncle*.—Medium.
*Color*.—Near Medium Yellow-Green 146D.

Berry:
*Size*.—Medium.
*Uniformity of size*.—Uniform.
*Berry weight*.—Medium, approximately 5.1 gr.
*Shape*.—Oval.
*Presence of seeds*.—Rudimentary.
*Cross section*.—Round.
*Dimensions*.—Longitudinal axis: Approximately 22 mm. Horizontal axis: Approximately 20 mm.
*Skin color (without bloom)*.—Near Dark Black 202A.
*Flesh color*.—Near Light Yellow-Green 145D.
*Juiciness of flesh*.—Slightly juicy.
*Berry firmness*.—Firm.
*Particular flavor*.—Slightly fruity.
*Bloom (cuticular wax)*.—Medium.
*Pedicel length*.—Medium, approximately 7.0 mm.
*Berry separation from pedicel*.—Medium.
*Visibility of hilum*.—Slightly.

Skin:
*Thickness*.—Medium.
*Texture*.—Smooth.
*Reticulation*.—Absent.
*Roughness*.—Absent.
*Tenacity*.—Tenacious to flesh.

Seed:
*Number of seeds per berry*.—Usually 1, sometimes 2.
*Size*.—Small.
*Color*.—Light green About 145C At first harvest but may darken over time.
*Texture*.—Medium.
*Endosperm*.—Slight.
*Fresh weight of seed-traces/berry*.—Approximately 2.37 mg.
*Room-dry weight of seed-traces/berry*.—Approximately 1.53 mg.

What is claimed is:

1. A new and distinct variety of grapevine plant as herein illustrated and described.

* * * * *

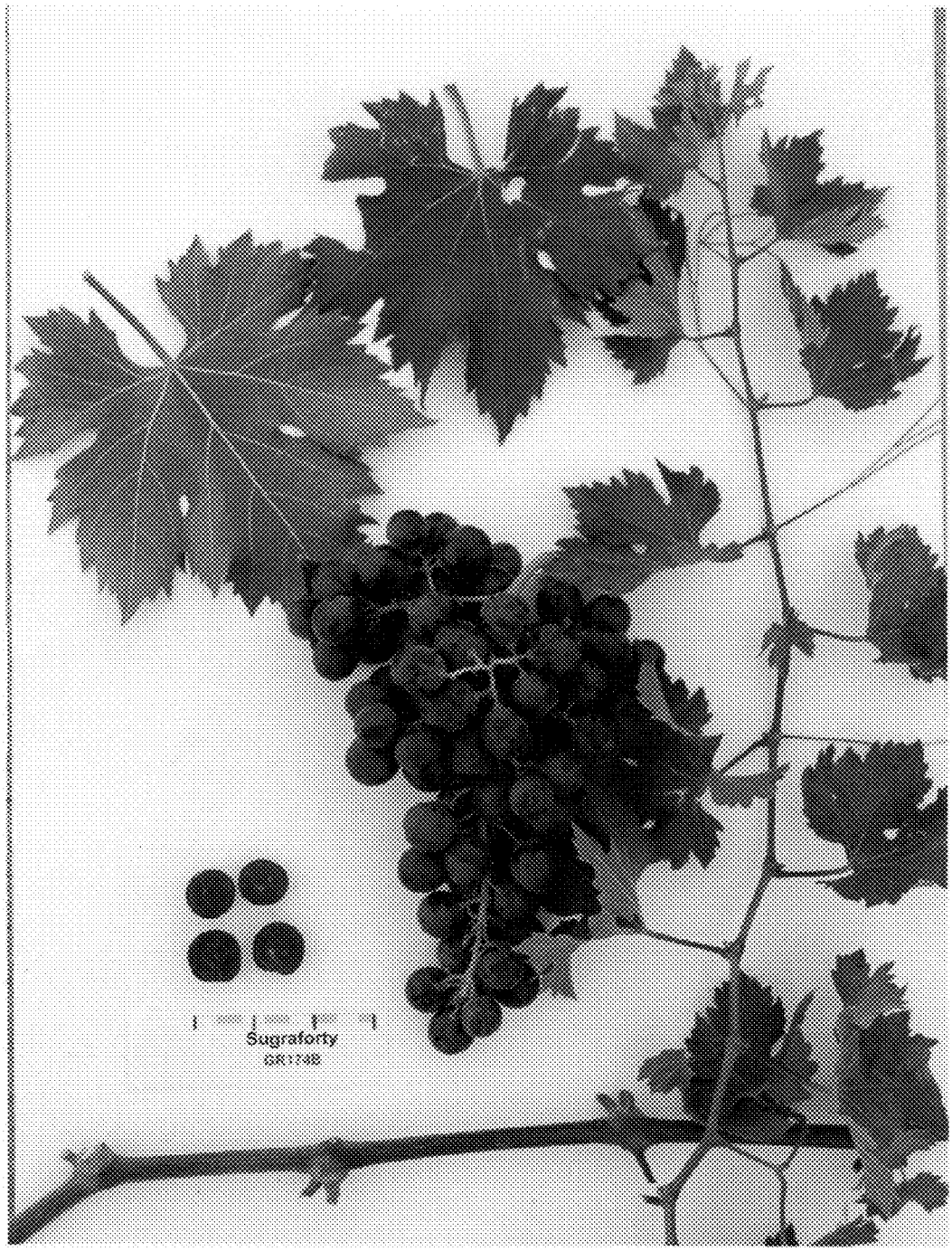
Sugraforty
SR1748